US006887993B1

(12) United States Patent
Tian et al.

(10) Patent No.: US 6,887,993 B1
(45) Date of Patent: *May 3, 2005

(54) 11-O-METHYLGELDANAMYCIN COMPOUNDS

(75) Inventors: Zong-Qiang Tian, Fremont, CA (US);
Yaoquan Liu, Castro Valley, CA (US);
David C. Myles, Kensington, CA (US);
Zhan Wang, El Dorado Hills, CA (US)

(73) Assignee: Kosan Biosciences, Inc., Hayward, CA (US)

( * ) Notice: Subject to any disclaimer, the term of this patent is extended or adjusted under 35 U.S.C. 154(b) by 6 days.

This patent is subject to a terminal disclaimer.

(21) Appl. No.: 10/826,445

(22) Filed: Apr. 16, 2004

Related U.S. Application Data

(60) Provisional application No. 60/519,479, filed on Nov. 12, 2003.

(51) Int. Cl.[7] .................... C07D 225/04; C07D 225/06
(52) U.S. Cl. .................................................. 540/461
(58) Field of Search ........................................ 540/461

(56) References Cited

U.S. PATENT DOCUMENTS

| | | | |
|---|---|---|---|
| 3,987,035 A | 10/1976 | Rinehart, Jr. et al. . | 260/239.3 P |
| 4,261,989 A | 4/1981 | Sasaki et al. ............... | 424/244 |
| 4,421,687 A | 12/1983 | Hasegawa et al. .... | 260/239.3 B |
| 4,421,688 A | 12/1983 | Muroi et al. .......... | 260/239.3 B |
| 4,540,517 A | 9/1985 | Tanida et al. ......... | 260/239.3 B |
| 5,387,584 A | 2/1995 | Schnur ........................ | 514/183 |
| 5,510,118 A | 4/1996 | Bosch et al. ................ | 424/489 |
| 5,534,270 A | 7/1996 | De Castro .................. | 424/490 |
| 5,662,883 A | 9/1997 | Bagchi et al. ................ | 424/9.4 |
| 5,932,566 A | 8/1999 | Schnur et al. .............. | 514/183 |
| 6,015,659 A | 1/2000 | Welch et al. ................ | 435/1.2 |
| 6,682,758 B1 | 1/2004 | Tabibi et al. ............... | 424/450 |
| 2003/0114450 A1 | 6/2003 | Santi et al. ............. | 514/234.5 |

FOREIGN PATENT DOCUMENTS

| | | |
|---|---|---|
| JP | 63-218620 | 9/1988 |
| JP | 04-046120 | 2/1992 |
| WO | WO 93/14215 A1 | 7/1993 |
| WO | WO 94/08578 A2 | 4/1994 |
| WO | WO 95/01342 A1 | 1/1995 |
| WO | WO 00/03737 A2 | 7/2000 |
| WO | WO 02/36574 A1 | 5/2002 |
| WO | WO 02/079167 A1 | 10/2002 |
| WO | WO 03/013430 A2 | 2/2003 |
| WO | WO 03/066005 A2 | 8/2003 |

OTHER PUBLICATIONS

Sasaki et al., *J. Antibiotics* 32 (8), 849–851 (1979), "Growth Inhibition of Virus Transformed Cells in Vitro and Antitumor Activity in Vivo of Geldanamycin and its Derivatives".

Muroi et al., *Tetrahedron* 37, 1123–1130 (1981), "The Structures of Macbecins I and II".

Omura et al., *J. Antibiotics* 37 (10), 1264–1267 (1984), "Chemical Modification and Antitumor Activity of Herbimycin A, 8,9–Epoxide, 7,9–Cyclic Carbamate, and 17– or 19–Amino Derivatives".

Shibata et al., *J. Antibiotics* 39 (11), 1630–1633 (1986), "The Structure and Cytocidal Acitivty of Herbimycin C".

Uehara et al., *J. Antibiotics* 41 (5), 831–834 (1988), "Effects of Herbimycin Derivatives on src Oncogene Function in Relation to Antitumor Activity".

Schnur et al., *J. Med. Chem.*, 38, 3806–3812 (1995), "Inhibition of Oncogene Products p185 (erbB–2) in vitro and in Vivo by Geldanamycin and Dihydrogeldanamycin Derivatives".

Schnur et al., *J. Med. Chem.*, 38, 3813–3820 (1995), "erbB–2 Oncogene Inhibition by Geldanamycin Derivatives: Synthesis, Mechanism of Action, and Structure–Activity Relationships".

Jez et al., *Chemistry & Biology*, 10, 361–368 (2003), "Crystal Structure and Molecular Modeling of 17–DMAG in Complex with Human Hsp90".

Carreras et al., *Anal. Biochem.*, 317 (1), 40–46 (Jun. 2003), "Filter Binding Assay for the Geldanamycin–Heat Shock Protein 90 Interaction".

Chemical Abstracts 110:231340 (abstract of JP 63–218620).
Chemical Abstracts 117:63002 (abstract of JP 04–046120).

*Primary Examiner*—Bruck Kifle
(74) *Attorney, Agent, or Firm*—Yuan Chao

(57) ABSTRACT

Compounds having a structure according to formula I

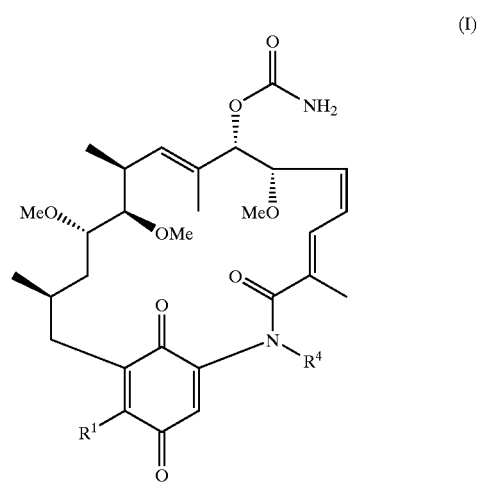

(I)

wherein the groups $R^1$ and $R^4$ are as defined in the specification, are useful as anti-proliferative agents.

1 Claim, No Drawings

11-O-METHYLGELDANAMYCIN COMPOUNDS

CROSS-REFERENCE TO RELATED APPLICATIONS

This application claims the benefit of U.S. Provisional Application No. 60/519,479, filed Nov. 12, 2003, the disclosure of which is incorporated herein by reference.

BACKGROUND OF THE INVENTION

1. Field of the Invention

This invention relates to 11-O-methylgeldanamycin compounds having cytotoxic properties, their method of preparation, and their use for treating hyperproliferative diseases, in particular cancer.

2. Description of Related Art

Geldanamycin belongs to the ansamycin family of natural products, whose members are characterized by a benzenoid nucleus (typically a benzoquinone or hydroquinone nucleus) connected at two meta positions to form a macrocyclic lactam. Besides geldanamycin, the ansamycins include the macbecins, the herbimycins, the TAN-420s, and reblastatin:

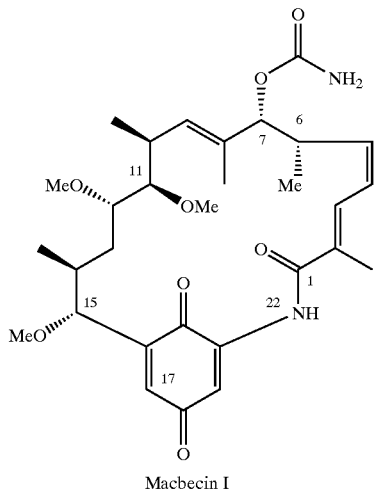

Macbecin I

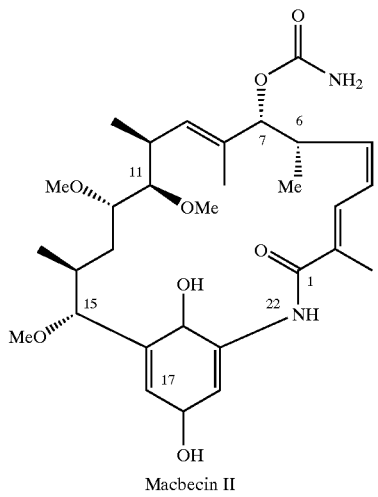

Macbecin II

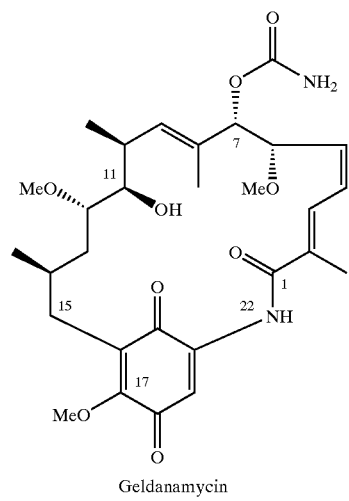

Geldanamycin

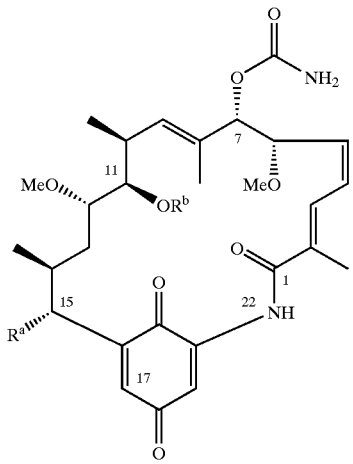

Herbimycins
A: $R^a$ = OMe  $R^b$ = Me
B: $R^a$ = H      $R^b$ = H
C: $R^a$ = OMe  $R^b$ = H

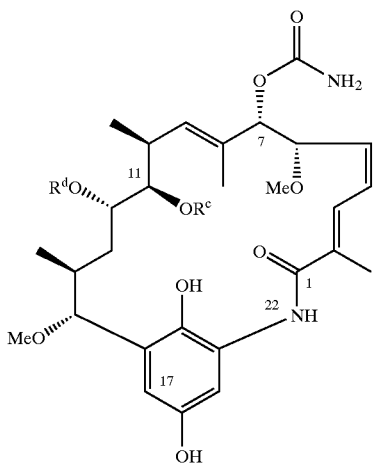

TAN-420
A: $R^c$ = H; $R^d$ = H
C: $R^c$ = H; $R^d$ = Me
E: $R^c$ = Me; $R^d$ = Me

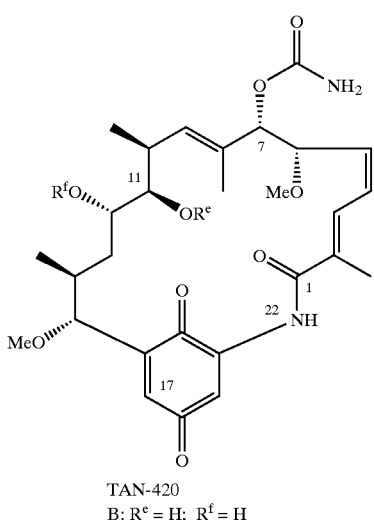

TAN-420
B: $R^e$ = H; $R^f$ = H
D: $R^e$ = H; $R^f$ = Me

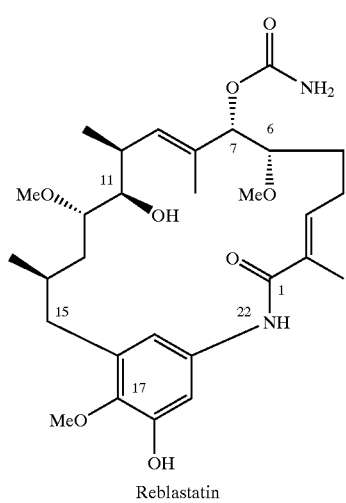

Reblastatin

Geldanamycin and its derivatives are the most extensively studied of the ansamycins. Although geldanamycin originally was identified as a result of screening for antibiotic activity, current interest in it is based primarily on its cytotoxicity towards tumor cells and, therefore, its potential as an anticancer agent. It is an inhibitor of heat shock protein-90 ("Hsp90"), which is involved in the folding, activation and assembly of a wide range of proteins ("client proteins"), including key proteins involved in signal transduction, cell cycle control and transcriptional regulation. The binding of geldanamycin to Hsp90 disrupts Hsp90-client protein interactions, preventing the client proteins from folding correctly and rendering them susceptible to proteasome-mediated destruction. Among the HSP90 client proteins are many mutated or overexpressed proteins implicated in cancer: p53, Bcr-Abl kinase, Raf-1 kinase, Akt kinase, Npm-Alk kinase $p185^{ErbB2}$ transmembrane kinase, Cdk4, Cdk6, Wee1 (a cell cycle-dependent kinase), HER2/Neu (ErbB2), and hypoxia inducible factor-1α(HIF-1α). However, the hepatotoxicity and poor bioavailability of geldanamycin have lead to its discontinuation as a clinical candidate.

Nevertheless, interest persists in the development of geldanamycin derivatives or analogs (collectively "geldanamycin compounds") having geldanamycin-like bioactivity, but with a better overall spectrum of properties. Position 17 of geldanamycin has been an attractive focal point, chemically speaking, for the synthesis of geldanamycin compounds because its methoxy group is readily displaced by a nucleophile, providing a convenient entry into 17-substituted-17-demethoxygeldanamycin compounds. Further, structure-activity relationship (SAR) studies have shown that structurally and sterically diverse 17-substituents can be introduced without destroying antitumor activity. See, e.g., Sasaki et at., U.S. Pat. No. 4,261,989 (1981); Schnur et al., U.S. Pat. No. 5,932,566 (1999); Schnur et al., J. Med. Chem., 38, 3806–3812 (1995); Schnur et al., J. Med. Chem., 38, 3813–3820 (1995); and Santi et al., US 2003/0114450 A1 (2003); the disclosures of which are incorporated by reference. The SAR inferences are supported by the X-ray crystal co-structure of the complex between Hsp90 and a geldanamycin derivative (17-DMAG, v. infra), showing that the 17-substituent projects out from the binding pocket and into the solvent (Jez et al., Chemistry& Biology, 10, 361–368 (2003)). Thus, position 17 is a choice one for the introduction of property-modulating substituents, such as a solubilizing group. The best-known 17-substituted geldanamycin is 17-allylamino-17-demethoxygeldanamycin ("17-AAG"), currently undergoing clinical trials. Another noteworthy 17-substituted geldanamycin is 17-(2-dimethyl-aminoethyl)amino-17-demethoxygeldanamycin ("17-DMAG") (Snader et al., WO 02/079167 A1 (2002), incorporated by reference).

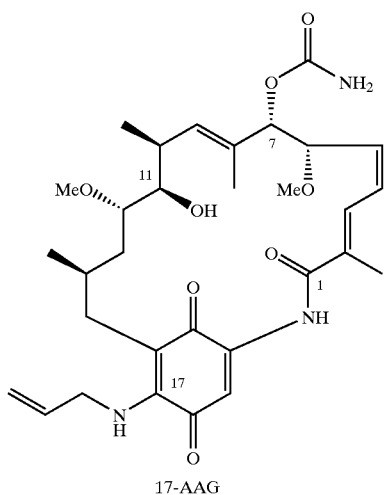

17-AAG

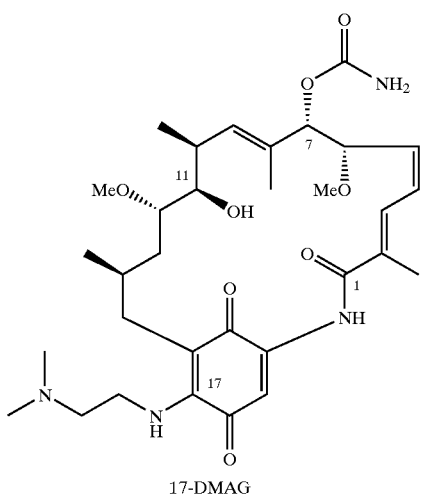

17-DMAG

The aforementioned X-ray co-crystal structure also shows that the 11-OH group is partially exposed to the solvent but still acts as an H-bond acceptor with Lys58 of Hsp90. We believe that a small ether group at position 11, such as an 11-OMe group, may retain the H-bonding capability while entering into other interactions with Hsp90, leading to compounds with improved physical and/or pharmacological properties.

The natural products herbimycin A, macbecins I and II and TAN-420E each have an 11-OMe group, but, during the course of their biosynthesis they also pick up a suite of idiosyncratic functionalities that are not found in geldanamycin, such as a 15-OMe group, which has a tendency to lower cytotoxic activity. More importantly, they lack geldanamycin's benzoquinone-bonded 17-OMe group. Without such a 17-OMe group, the introduction of 17-substituents is more difficult. See Muroi et al., Tetrahedron 37, 1123–1130 (1981); Shibata et al., J. Antibiotics 39 (11), 1630–1633 (1986); Tanida et al., U.S. Pat. No. 4,540,517 (1985).

The literature also contains a number of disclosures relating to semi-synthetic geldanamycin compounds having a group other than hydroxyl at position C11: Muroi et al., U.S. Pat. No. 4,421,688 (1983); Schnur, U.S. Pat. No. 5,387,584 (1995); Schnur et al., U.S. Pat. No. 5,932,566 (1999); Welch et al., U.S. Pat. No. 6,015,659 (2000); Whitesell et al., WO 94/08578 A2 (1994); Ho et al., WO 00/03737 A2 (2000); Snader et al., WO 02/36574 A1 (2002); Snader et al., WO 02/079167 A1 (2002); Santi et al., WO 03/013430 A2 (2003); Zhang et al., WO 03/066005 A2 (2003); Omura et al., JP 63-218620 (1988); Schnur et al., J. Med. Chem., 38, 3806–3812 (1995); and Schnur et al., J. Med. Chem., 38, 3813–3820 (1995); the disclosures of which are incorporated herein by reference. Some of these references describe the preparation of specific geldanamycin compounds having the 11-OH group replaced by another functionality (e.g., fluoro, acyl, sulfonyl, allyl). Others disclose a generic formula showing a range of functionalities at position C11, but without providing any particulars on how they might be introduced. Thus, the prior art is devoid of specific disclosures relating to the chemical synthesis of 11-O-methylgeldanamycin compounds.

BRIEF SUMMARY OF THE INVENTION

The present invention provides 11-O-methylgeldanamycin compounds having a structure according to formula I:

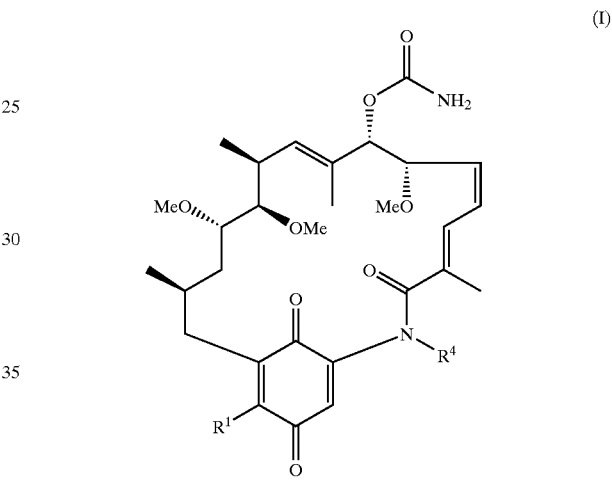

(I)

and the pharmaceutically acceptable salts, esters, and prodrug forms thereof wherein $R^1$ is OMe or $R^2R^3N$, where $R^2$ and $R^3$ are independently H, $C_1$–$C_8$ alkyl, $C_2$–$C_8$ alkenyl, $C_2$–$C_8$ alkynyl, cycloalkyl, heterocyclo, aryl, or heteroaryl; or $R^2$ and $R^3$ and the nitrogen to which they are attached combine to form a substituted or unsubstituted 3, 4, 5, 6, or 7 membered ring; and $R^4$ is H or $CH_2C(=O)R^5$, where $R^5$ is a substituted or unsubstituted phenyl group.

In another embodiment, this invention provides a method of inhibiting the proliferation of a target cell, comprising contacting the target cell with an effective amount of a compound having a structure according to formula I. The target cell can be a cancer cell, especially a breast cancer, lung cancer, ovarian cancer, or leukemia cell.

In another embodiment, this invention provides a method of treating a hyperproliferative disease, comprising administering to a patient suffering from such hyperproliferative disease a therapeutically effective amount of a compound having a structure according to formula I. The hyperproliferative disease so treated may be cancer, especially breast cancer, lung cancer, ovarian cancer, or leukemia.

In another embodiment, this invention provides for the use of a compound having a structure according to formula I for the preparation of a medicament for treating a hyperproliferative disease, which may be cancer, especially breast cancer, lung cancer, ovarian cancer, or leukemia.

DETAILED DESCRIPTION OF THE INVENTION

Definitions

"Alkyl" means an optionally substituted straight or branched chain hydrocarbon moiety having the specified number of carbon atoms in the chain (e.g., as in "$C_1$–$C_8$ alkyl") or, where the number of carbon atoms is not specified, up to 5 carbon atoms in the chain.

"Alkenyl" means an optionally substituted straight or branched chain hydrocarbon moiety having at least one carbon-carbon double bond and the specified number of carbon atoms in the chain (e.g., as in "$C_2$–$C_8$ alkenyl") or, where the number of carbon atoms is not specified, up to 5 carbon atoms in the chain.

"Alkynyl" means an optionally substituted straight or branched chain hydrocarbon moiety having at least one carbon-carbon triple bond and the specified number of carbon atoms in the chain (e.g., as in "$C_2$–$C_8$ alkynyl") or, where the number of carbon atoms is not specified, up to 5 carbon atoms in the chain.

"Alkylaryl," "arylalkyl," "heterocycloalkyl," "alkylheteroaryl," "alkylheterocycle" and the like mean an aryl, heterocyclic, or heteroaryl group, as the case may be, bonded directly to an alkyl moiety, as in benzyl, phenethyl, and the like.

"Aryl" means a monocyclic or bicyclic aromatic hydrocarbon ring system having 6 to 12 carbon atoms in the ring portion, such as phenyl, napthyl, and biphenyl moieties, each of which is optionally substituted at one or more positions.

"Cycloalkyl" means an optionally substituted, saturated cyclic hydrocarbon ring system, preferably containing 1 to 3 rings and 3 to 7 carbons per ring which may be further fused with an unsaturated $C_3$–$C_7$ carbocyclic ring. Exemplary cycloalkyl ring systems include cyclopropyl, cyclobutyl, cyclopentyl, cyclohexyl, cycloheptyl, cyclooctyl, cyclodecyl, cyclododecyl, and adamantyl.

"Halogen" or "halo" means fluorine, chlorine, bromine and iodine.

"Heterocycle", "heterocyclic," or "heterocyclo" means an optionally substituted, fully saturated or unsaturated, aromatic or nonaromatic ring system, for example, which is a 4 to 7 membered monocyclic, 7 to 11 membered bicyclic, or 10 to 15 membered tricyclic ring system, which has at least one heteroatom in at least one carbon atom-containing ring. "Heteroaryl" means a heterocycle in which the ring system is aryl. Each ring of the heterocyclic group containing a heteroatom may have 1, 2 or 3 heteroatoms selected from N, O and S, where the N and S optionally may be oxidized and the N optionally may be quaternized.

Exemplary monocyclic heterocyclic ring systems include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thizaolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridinyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1,1-dioxothienyl, dioxanyl, isothiazolidinyl, thietanyl, thiiranyl, triazinyl, and triazolyl, and the like. Preferred heterocyclo groups include pyridinyl, pyrazinyl, pyrimidinyl, pyrroyl, pyrazolyl, imidazolyl, thiazolyl, oxazolyl, isoxazolyl, thiadiazolyl, oxadiazolyl, thienyl, furanyl, quinolinyl, isoquinolinyl, and the like.

Where it is indicated that a group may be substituted, for example by use "substituted or unsubstituted" or "optionally substituted" phrasing, such group may have one or more independently selected substituents, preferably one to five in number, more preferably one or two in number. It is understood that substituents and substitution patterns can be selected by one of ordinary skill in the art to provide compounds that are chemically stable and that can be synthesized by techniques known in the art as well as the methods set forth herein. Examples of suitable substituents include alkyl, alkenyl, alkynyl, aryl, halo, trifluoromethoxy, trifluoromethyl, hydroxy, alkoxy, cycloalkyloxy, heterocyclooxy, alkanoyl, alkanoyloxy, amino, alkylamino quarternary ammonium, aralkylamino, cycloalkylamino, heterocycloamino, dialkylamino, alkanoylamino, thio, alkylthio, cycloalkylthio, heterocyclothio, ureido, nitro, cyano, carboxy, caroboxylalkyl, carbamyl, alkoxycarbonyl, alkylthiono, arylthiono, alkylsulfonyl, sulfonamindo, aryloxy, and the like, in addition to those specified herein. The substituent may be further substituted, e.g., by halo, hydroxy, alkyl, alkoxy; aryl, substituted aryl, substituted alkyl, substituted aralkyl, and the like.

"Pharmaceutically acceptable ester" means an ester that hydrolyzes in vivo (for example in the human body) to produce the parent compound or a salt thereof or has per se activity similar to that of the parent compound. Suitable ester groups include, without limitation, those derived from pharmaceutically acceptable aliphatic carboxylic acids, particularly alkanoic, alkenoic, cycloalkanoic and alkanedioic acids, in which each alkyl or alkenyl moiety preferably has no more than six carbon atoms. Illustrative esters include formates, acetates, propionates, butyrates, acrylates, citrates, succinates, and ethylsuccinates.

"Pharmaceutically acceptable salt" means a salt of a compound suitable for pharmaceutical formulation. Suitable pharmaceutically acceptable salts include acid addition salts which may, for example, be formed by mixing a solution of a compound with a solution of a pharmaceutically acceptable acid such as hydrochloric acid, hydrobromic acid, sulfuric acid, fumaric acid, maleic acid, succinic acid, benzoic acid, acetic acid, citric acid, tartaric acid, phosphoric acid, carbonic acid, or the like. Where a compound carries one or more acidic moieties, pharmaceutically acceptable salts may be formed by treatment of a solution of the compound with a solution of a pharmaceutically acceptable base, such as lithium hydroxide, sodium hydroxide, potassium hydroxide, tetraalkylammonium hydroxide, lithium carbonate, sodium carbonate, potassium carbonate, ammonia, alkylamines, or the like.

The present invention includes within its scope prodrugs of the compounds of this invention. Such prodrugs are in general functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to a subject in need thereof. Conventional procedures for the selection and preparation of suitable prodrug derivatives are described, for example, in *Design of Prodrugs*, Bundgaard, ed., Elsevier, 1985.

Unless particular stereoisomers are specifically indicated (e.g., by a bolded or dashed bond at a relevant stereocenter in a structural formula), all stereoisomers are included within the scope of the invention, as pure compounds as well as mixtures thereof. Unless otherwise indicated, individual enantiomers, diastereomers, geometrical isomers, and combinations and mixtures thereof are all encompassed by the present invention. Polymorphic crystalline forms and solvates are also encompassed within the scope of this invention.

Compounds and Methods

Geldanamycin is a well-known natural product, obtainable by culturing the producing organism, *Streptomyces hygroscopicus* var. *geldanus* NRRL 3602. The compounds of this invention can be made semi-synthetically, by chemical modification of geldanamycin.

Turning to embodiments within formula I, in one embodiment $R^4$ is H while $R^1$ is as defined in the BRIEF SUMMARY OF THE INVENTION section, above.

In another embodiment $R^1$ is $R^2R^3N$. Preferably, in this embodiment $R^4$ is H.

In another embodiment, $R^1$ is MeO. Preferably, in this embodiment $R^4$ is H.

In another embodiment, $R^1$ is $R^2R^3N$, where $R^2$ is H and $R^3$ is a substituted $C_1$–$C_3$ alkyl (preferably a substituted $C_2$ alkyl group). The substituent preferably is selected from the group consisting of fluoro, cycloalkylamino, dialkylamino, heterocyclo having at least one nitrogen ring atom, and heteroaryl having at least one nitrogen ring atom. Preferably, in this embodiment $R^4$ is H.

In another embodiment, $R^1$ is $R^2R^3N$, where $R^2$ is H and $R^3$ is a $C_2$–$C_4$ alkenyl group, preferably allyl. Preferably, in this embodiment $R^4$ is H.

In another embodiment, $R^1$ is $R^2R^3N$, where $R^2$ and $R^3$ are each H. Preferably, in this embodiment $R^4$ is H.

In another embodiment, $R^1$ is $R^2R^3N$, where $R^2$ and $R^3$ and the nitrogen to which they are attached combine to form a substituted or unsubstituted 3, 4, 5, 6, or 7 membered ring (preferably a 3, 4, 5, or 6 membered ring). Preferably, in this embodiment $R^4$ is H.

Specific compounds having a structure according to formula I include those in which $R^1$ is as shown in Table 1 below and $R^4$ is H:

Thus, $R^1$ may be selected from the group consisting of

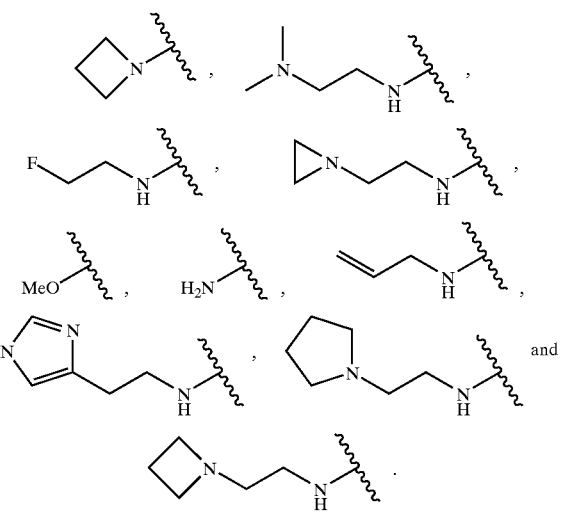

The full structures of compounds I-a through I-j are as follows:

(I-a)
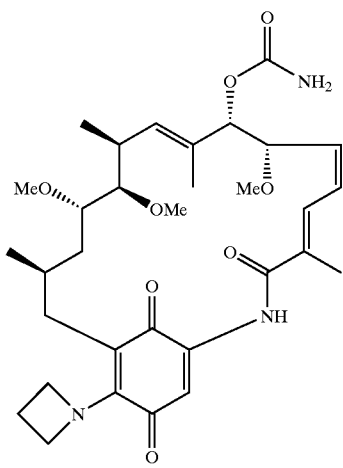
(I-b)
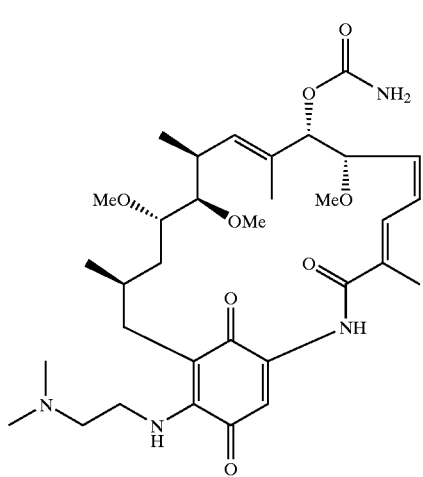
(I-c)
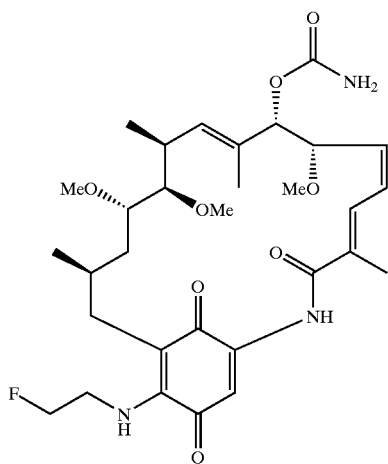
(I-d)
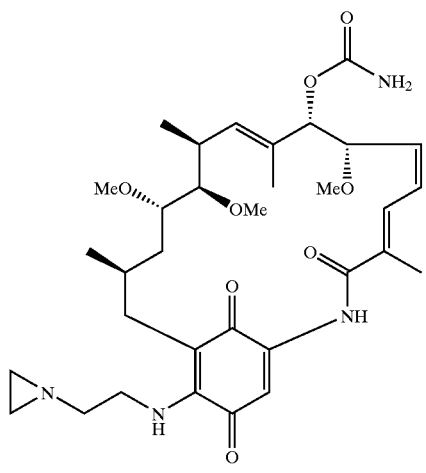
(I-e)
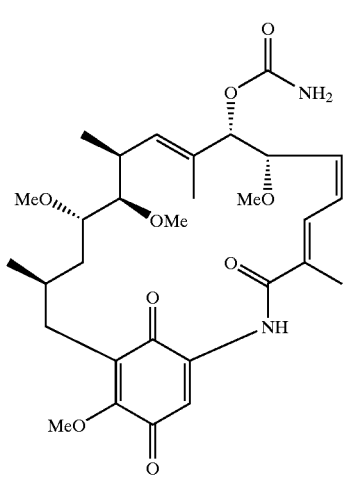
(I-f)
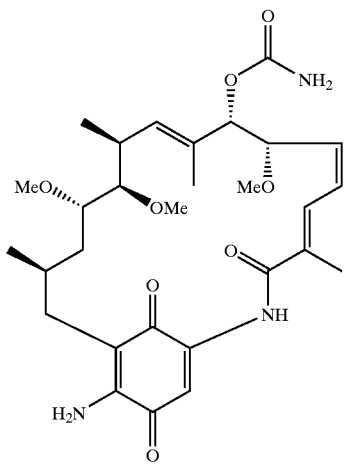

(I-g)

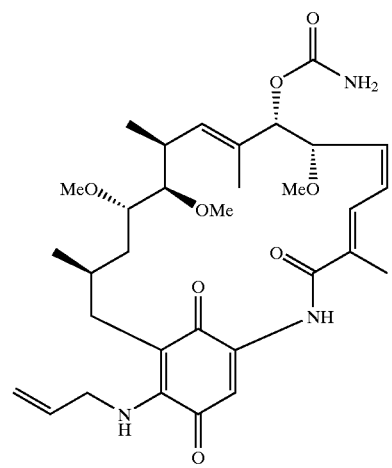

(I-h)

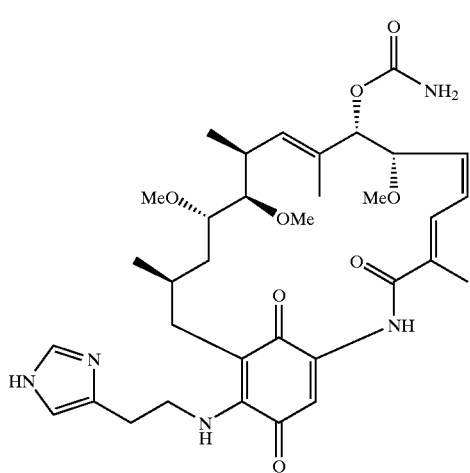

(I-i)

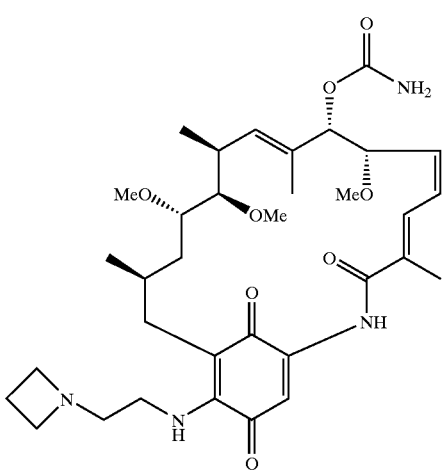

(I-j)

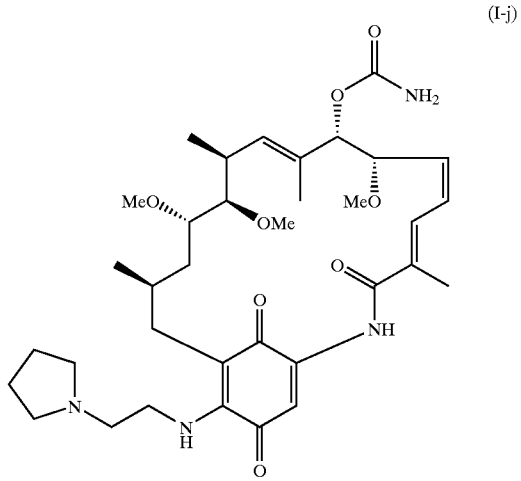

Compounds I can be made by either one of two methods. In Method A, shown in Scheme 1 (depicting the instance in which R⁴ is H), geldanamycin is first converted to compound I-e (11-O-methyl-geldanamycin) by treatment with trimethyloxonium tetrafluoroborate. Compound I-e is then converted to other compounds I of this invention (those in which the group $R^1$ is $R^2R^3N$) by treatment with the corresponding amine $R^2R^3NH$.

Scheme 1

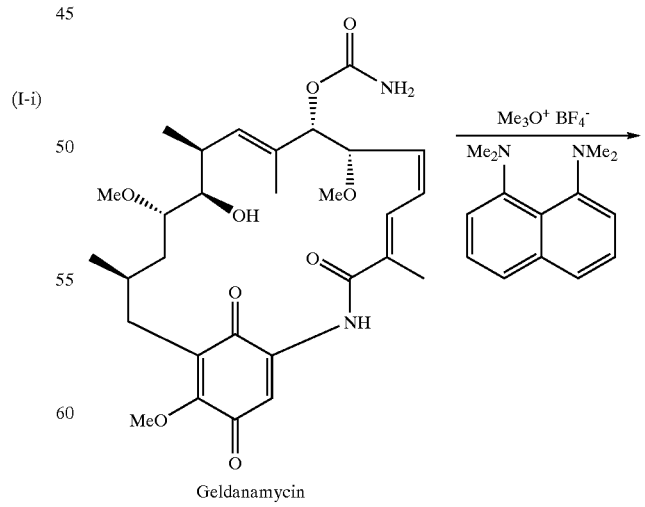

Geldanamycin

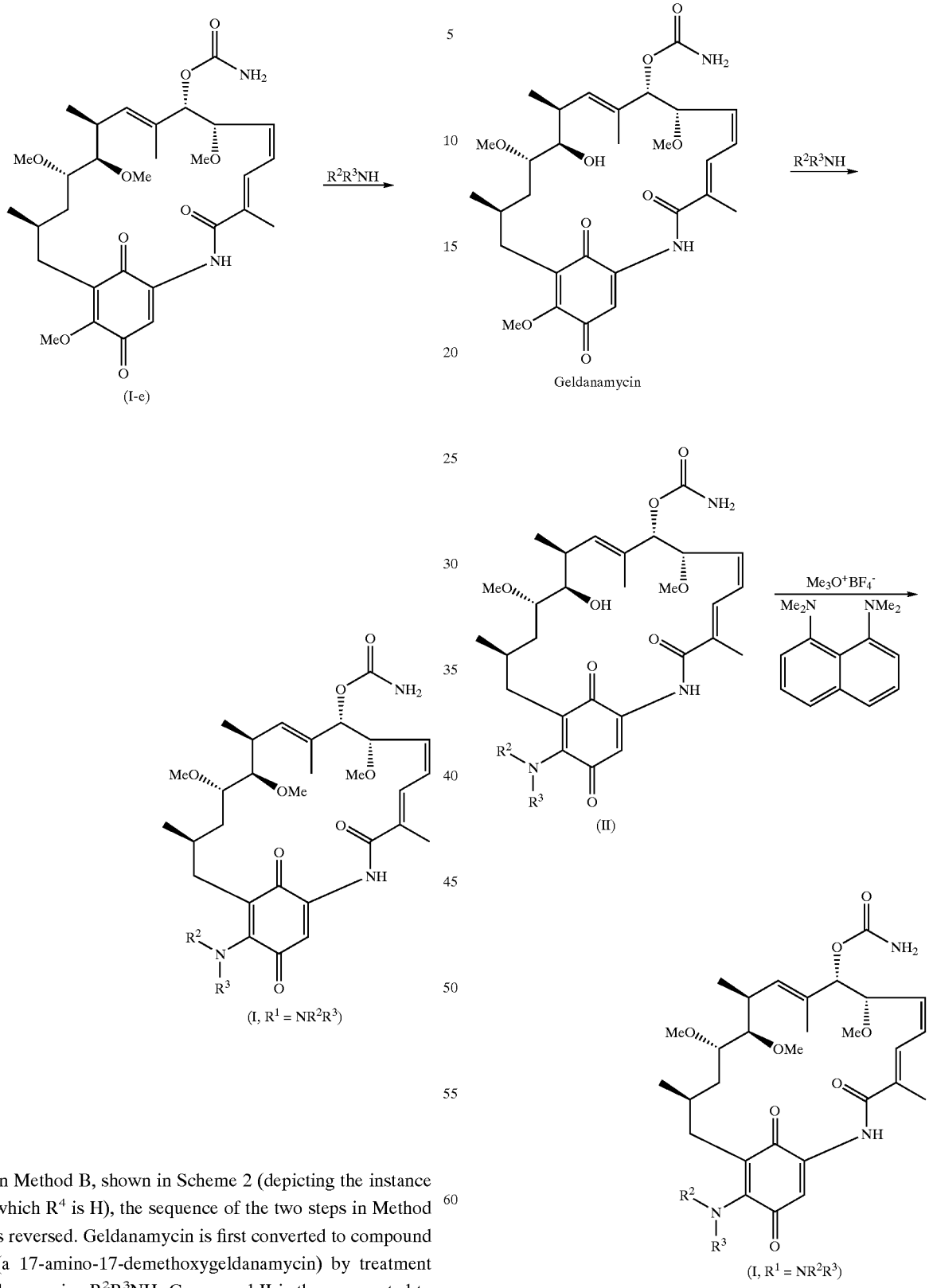

In Method B, shown in Scheme 2 (depicting the instance in which $R^4$ is H), the sequence of the two steps in Method A is reversed. Geldanamycin is first converted to compound II (a 17-amino-17-demethoxygeldanamycin) by treatment with an amine $R^2R^3NH$. Compound II is then converted to a compound I (wherein $R^1$ is $R^2R^3N$) by treatment with trimethyloxonium tetrafluoroborate.

Those skilled in the art will appreciate that some compounds I can be made by either Method A or Method B but that other compounds I, having a group $R^2$ or $R^3$ that is susceptible to methylation by trimethyloxonium tetrafluoroborate, are more suitably made by Method A.

Compounds where $R^4$ is $CH_2C(C=O)R^5$ can be made by alkylation of the nitrogen at position 22 ("N22") with an alkylating group. Where Method A is employed, alkylation is preferably performed at the stage of compound I-e (i.e., before displacement of the 17-OMe group with an amine $R^2R^3NH$), to avoid the simultaneous alkylation of either the $R^2$ or $R^3$ group, if they are susceptible to alkylation. Of course, if neither the $R^2$ nor the $R^3$ group is susceptible to alkylation, then N22 alkylation after completion of the second step shown in Scheme I is viable. Where Method B is used, the groups $R^2$ and $R^3$ should be not susceptible to alkylation (vide supra), so that N22 alkylation can be performed either before or after 17-OMe displacement.

Generally, N22 alkylation can be accomplished by treatment with a base such as an alkoxide in a polar solvent such as DMF or DMSO, followed by addition of a desired phenacyl halide, at 5 to 65° C. Or, alkylation can be accomplished by refluxing in acetone in the presence of anhydrous potassium carbonate and the phenacyl halide. N22 alkylation is further described in Schnur et al., U.S. Pat. No. 5,932,566 (1999), the disclosure of which is incorporated by reference.

The present invention also includes methods for treating diseases such as, but not limited to, hyperproliferative diseases, including: cancers of the head and neck which include tumors of the head, neck, nasal cavity, paranasal sinuses, nasopharynx, oral cavity, oropharynx, larynx, hypopharynx, salivary glands, and paragangliomas; cancers of the liver and biliary tree, particularly hepatocellular carcinoma; intestinal cancers, particularly colorectal cancer; treat ovarian cancer; small cell and non-small cell lung cancer; breast cancer sarcomas, such as fibrosarcoma, malignant fibrous histiocytoma, embryonal rhabdomyosarcoma, leiomysosarcoma, neurofibrosarcoma, osteosarcoma, synovial sarcoma, liposarcoma, and alveolar soft part sarcoma; neoplasms of the central nervous systems, particularly brain cancer; lymphomas such as Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma. Clinically, practice of the methods and use of compositions described herein will result in a reduction in the size or number of the cancerous growth and/or a reduction in associated symptoms (where applicable). Pathologically, practice of the method and use of compositions described herein will produce a pathologically relevant response, such as: inhibition of cancer cell proliferation, reduction in the size of the cancer or tumor, prevention of further metastasis, and inhibition of tumor angiogenesis. The method of treating such diseases comprises administering a therapeutically effective amount of an inventive combination to a subject. The method may be repeated as necessary.

The methods and compositions of the present invention can be used in combination therapies. In other words, the inventive compounds and compositions can be administered concurrently with, prior to, or subsequent to one or more other desired therapeutic or medical procedures. The particular combination of therapies and procedures in the combination regimen will take into account compatibility of the therapies and/or procedures and the desired therapeutic effect to be achieved. Thus, the compositions described herein can be combined with other treatment modalities, such as surgery and/or radiation. In some embodiments of the present invention, an agent or procedure is further included to mitigate potential side effects from the inventive compound or composition such as diarrhea, nausea and vomiting. Diarrhea may be treated with antidiarrheal agents such as opioids (e.g. codeine, diphenoxylate, difenoxin, and loeramide), bismuth subsalicylate, and octreotide. Nausea and vomiting may be treated with antiemetic agents such as dexamethasone, metoclopramide, diphenyhydramine, lorazepam, ondansetron, prochlorperazine, thiethylperazine, and dronabinol.

In one preferred combination therapy, compounds of this invention are administered in combination with other anti-cancer or cytotoxic agents, including other Hsp90 inhibitors; microtubule stabilizers, intercalators, DNA crosslinkers, alkylating agents, antimetabolites, angiogenesis inhibitors, topoisomerase inhibitors, nucleoside analogs, and tyrosine kinase inhibitors. Specific anti-cancer agents that can be so used in combination include geldanamycin, 17-AAG, 17-DMAG, epothilones, discodermolide, paclitaxel, docetaxel, imatinib, gefitinib, vinca alkaloids (vinblastine, vincristine), mitomycin C, bicalutamide, cisplatin, fluoruracil, gemcitabine, irinotecan, methotrexate, capecitabine, doxorubicin, floxuridine, oxaliplatin, cisplatin, bleomycin, busulfan, hydroxyurea, thiotepa, camptothecin, interferons, interleukins, and the like.

In particular, the co-administered anti-cancer or cytotoxic agent can be a protein kinase inhibitor, including: quinazolines, particularly 4-anilinoquinazolines such as Iressa (AstraZeneca; N-(3-chloro-4-fluorophenyl)-7-methoxy-6[3-(4-morpholinyl)propoxy]4-quinazolinamine) and Tarceva (Roche/Genentech; N-(3-ethynylphenyl)-6,7-bis(2-methoxyethoxy)-4-quinazolinamine monohydrochloride); phenylamino-pyrimidines such as Gleevec (Novartis; 4-[(4-methyl-1-piperazinyl)methyl]-N-[4-methyl-3-[[4-3-pyridinyl)-2-pyrimidinyl]amino]phenyl] benzamide); pyrrolo- and pyrazolopyrimidines such as BIBX 1382 (Boehringer Ingelheim; N8-(3-chloro-4-fluorophenyl)-N-2-(1-methyl-4-piperidinyl)-pyrimido[5,4-d]pyrimidine-2,8-diamine); indoles and oxindoles such as Semaxinib (Pharmacia; 3-[(3,5-dimethyl-1H-pyrrol-2-yl) methylene]-1,3-dihydro-2H-Indol-2-one); benzylidene malononitriles; flavones such as flavopiridol (Aventis; 2-(2-chlorophenyl)-5,7-dihydroxy-8[(3S,4R)-3-hydroxy-1-methyl-4-piperidinyl]-4H-1-benzopyran-4-one); staurosporines such as CEP-701 (Cephalon); antibodies such as Herceptin (Genentech); and ribozymes such as Angiozyme (Ribozyme Pharmaceuticals).

In another aspect of the present invention, non-cancer disorders that are characterized by cellular hyperproliferation are treated. Illustrative examples of such disorders include but are not limited to: atrophic gastritis, inflammatory hemolytic anemia, graft rejection, inflammatory neutropenia, bullous pemphigoid, coeliac disease, demyelinating neuropathies, dermatomyositis, inflammatory bowel disease (ulcerative colitis and Crohn's disease), multiple sclerosis, myocarditis, myositis, nasal polyps, chronic sinusitis, pemphigus vulgaris, primary glomerulonephritis, psoriasis, surgical adhesions, stenosis or restenosis, scleritis, scieroderma, eczema (including atopic dermatitis. irritant dermatitis, allergic dermatitis), periodontal disease (i.e., periodontitis), polycystic kidney disease, and type I diabetes. Other examples include vasculitis (e.g., Giant cell arteritis (temporal arteritis, Takayasu's arteritis), polyarteritis nodosa, allergic angiitis and granulomatosis (Churg-Strauss disease), polyangitis overlap syndrome, hypersensitivity vasculitis (Henoch-Schonlein purpura), serum sickness, drug-induced vasculitis, infectious vasculitis, neoplastic vasculitis, vasculitis associated with connective tissue disorders, vasculitis associated with congenital deficiencies of the complement system, Wegener's granulomatosis, Kawasaki's disease, vasculitis of the central nervous system, Buerger's disease and systemic sclerosis); gastrointestinal tract diseases (e.g., pancreatitis, Crohn's disease, ulcerative colitis, ulcerative proctitis, primary sclerosing cholangitis, benign strictures of any cause including ideopathic (e.g., strictures of bile ducts, esophagus, duodenum, small bowel or colon); respiratory tract diseases (e.g., asthma, hypersensitivity pneumonitis, asbestosis, silicosis and other forms of pneumoconiosis, chronic bronchitis and chronic obstructive airway disease); nasolacrimal duct diseases (e.g., strictures of all causes including ideopathic); and eustachean tube diseases (e.g., strictures of all causes including ideopathic).

For human administration, an effective amount of a compound of this invention is used, optionally in combination with a pharmaceutically acceptable carrier. The composition may be dry, or it may be a solution. Treatment may be reactive, for treating an existing condition, or prophylactic, to forestall development of a condition. Compounds of this invention can be used in the preparation of a medicament. The compounds may be administered orally, topically, or parenterally (e.g., intravenously, subcutaneously, intraperitoneally, transdermally).

Compounds of this invention may be used in a composition, combined with a pharmaceutically acceptable carrier. The compounds may be in their free forms or, where appropriate, as a pharmaceutically acceptable derivatives such as prodrugs, and saltsand esters thereof.

The composition may be in any suitable form such as solid, semisolid, or liquid form. In general, the pharmaceutical preparation will contain one or more of the compounds of the invention as an active ingredient in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, pessaries, solutions, emulsions, suspensions, and any other form suitable for use. The carriers that can be used include water, glucose, lactose, gum acacia, gelatin, mannitol, starch paste, magnesium trisilicate, talc, corn starch, keratin, colloidal silica, potato starch, urea, and other carriers suitable for use in manufacturing preparations, in solid, semi-solid, or liquified form. In addition, auxiliary stabilizing, thickening, and coloring agents and perfumes may be used.

Where applicable, compounds of this invention may be formulated as microcapsules and nanoparticles. General protocols are described for example, in Bosch et al., U.S. Pat. No. 5,510,118 (1996); De Castro, U.S. Pat. No. 5,534, 270 (1996); and Bagchi et al., U.S. Pat. No. 5,662,883 (1997), which are all incorporated herein by reference. By increasing the ratio of surface area to volume, these formulations allow for the oral delivery of compounds that would not otherwise be amenable to oral delivery.

Dosage levels of the compounds of the present invention are of the order from about 0.1 mg to about 100 mg per kilogram of body weight per day, preferably from about 1 mg to about 50 mg per kilogram of body weight per day. More preferably, the dosage levels are from about 5 mg to about 20 mg per kilogram of body weight per day, corresponding to 350 mg to 1400 mg per patient per day, assuming a 70 kg patient. In addition, the compounds of the present invention may be administered on an intermittent basis, i.e., at semi-weekly, weekly, semi-monthly, or monthly intervals.

The amount of active ingredient that may be combined with the carrier materials to produce a single dosage form will vary depending upon the host treated and the particular mode of administration. For example, a formulation intended for oral administration to humans may contain carrier material, which may vary from about 5 percent to about 95 percent of the total composition. Dosage unit forms will generally contain from about 5 mg to about 500 mg of active ingredient.

It will be understood, however, that the specific dose level for any particular patient will depend on a variety of factors. These factors include the activity of the specific compound employed; the age, body weight, general health, sex, and diet of the subject; the time and route of administration and the rate of excretion of the drug; whether a drug combination is employed in the treatment; and the severity of the particular disease or condition for which therapy is sought.

The practice of this invention can be further understood by reference to the following examples, which are provided by way of illustration and not of limitation.

EXAMPLE 1

Synthesis of Compounds by Method A

The following description of Method A is applicable to the synthesis of compounds of this invention.

To a suspension of geldanamycin (1 equiv.) in dichloromethane (20 mL per mmol of geldanamycin) is added trimethyloxonium tetrafluoroborate (3 equiv.) and N,N, N',N'-tetramethylnaphthalene-1,8-diamine (3.5 equiv). After stirring at 40° C. for 2 h, the suspension was diluted with ethyl acetate and washed sequentially with 0.1 M aqueous hydrochloric acid, saturated aqueous sodium bicarbonate solution, and saturated aqueous sodium chloride. The organic solution was dried over anhydrous sodium sulfate, filtered, and evaporated to dryness, giving a brown solid. Purification by flash chromatography on silica gel (eluted using mixed dichloromethane/ethyl acetate/methanol solvents) gave 11-O-methyl-geldanamycin (compound I-e) as a yellow solid. Electrospray ionization time-of-flight mass spectrometry ("ESI TOF MS") m/z 597.2770, calc'd for $C_{30}H_{42}N_2O_9Na[M+Na]^+$, 597.2783. $^{13}C$ NMR (CDCl$_3$, 100 MHz) δ (relative to CDCl$_3$ at 77.0 ppm) 12.2, 13.9, 16.0, 21.5, 29.5, 32.5, 33.7, 36.5, 56.2, 57.4, 59.4, 61.5, 78.9, 79.4, 81.7, 83.3, 111.0, 125.7, 128.1, 130.5, 131.9, 134.5, 136.6, 137.8, 155.9, 156.9, 168.6, 183.9, 184.1.

Conversion of 11-O-methylgeldanamycin to other compounds I was effected as follows: To a solution of 11-O-methylgeldanamycin (1 equiv.) in 1,2-dichloroethane was added an amine $R^2R^3NH$ (1-2 equiv.). (Triethylamine was used to release the amine in case its hydrochloride salt was used). The mixture was stirred at 20° C. until the reaction was complete as monitored by TLC. The mixture was concentrated on a rotary evaporator, re-suspended in ethyl acetate, washed sequentially with water, saturated aqueous sodium bicarbonate, and saturated aqueous sodium chloride. The organic solution was dried over anhydrous sodium sulfate, filtered, and evaporated to dryness. The crude product was purified by HPLC on a C-18 column, eluted using a gradient of water/acetonitrile containing 0.1% (v) acetic acid. The 11-O-methyl-17-(substituted)amino-17-demethoxygeldanamycin product (compound I, $R^1$ equals $R^2R^3N$) was obtained as a purple solid.

EXAMPLE 2

Synthesis of Compounds by Method B

The following description of Method B is applicable to the synthesis of compounds of this invention.

To a solution of geldanamycin (1 equiv.) in 1,2-dichloroethane was added an amine $R^2R^3NH$ (~2 equiv.) (Triethylamine was used to release the amine in case its hydrochloride salt was used). The mixture was stirred at 20° C. until the reaction was complete as monitored by TLC. The mixture was concentrated on a rotary evaporator, re-suspended in ethyl acetate, washed sequentially with water, saturated aqueous sodium bicarbonate, and saturated aqueous sodium chloride. The organic solution was dried over anhydrous sodium sulfate, filtered, and evaporated to dryness. The crude product was purified by flash chromatography on silica gel (eluted using 1~10% methanol in dichloromethane). The 17-(substituted)amino-17-demethoxygeldanamycin product (compound II) was obtained as a purple solid.

To a solution of 17-(substituted)amino-17-demethoxygeldanamycin (compound II, 1 equiv.) in dichloromethane (20 mL per mmol of geldanamycin) was added trimethyloxonium tetrafluoroborate (3 equiv.) and N,N,N',N'-tetramethyl-naphthalene-1,8-diamine (3.5 equiv). After stirring at 40° C. for 2 h, the suspension was diluted with ethyl acetate and washed sequentially with 0.1 M aqueous hydrochloric acid, saturated aqueous sodium bicarbonate, and saturated aqueous sodium chloride. The organic solution was dried over anhydrous sodium sulfate, filtered, and evaporated to dryness. The crude product was purified by HPLC on a C-18 column eluted using a gradient of water/acetonitrile. The 11-O-methyl-17-(substituted)amino-17-demethoxygeldanamycin product (compound I, $R^1$ equals $R^2R^3N$) was obtained as a purple solid.

EXAMPLE 3

Compound I-a

Compound I-a (11-O-methyl-17-(1-azetidinyl)-17-demethoxygeldanamycin) was made by both the general procedures of Method A and Method B: ESI TOF MS m/z 622.3094; calc'd for $C_{32}H_5N_3O_8Na[M+Na]^+$, 622.3099. $^{13}C$ NMR (CDCl$_3$, 100 MHz) δ 12.3, 14.1, 16.4, 18.5, 21.5, 30.0, 33.6, 33.9, 36.3, 56.1, 57.6, 58.4 (2C), 59.8, 78.7, 79.6, 82.0, 83.5, 108.7, 109.4, 125.9, 127.8, 129.9, 132.1, 134.9, 136.3, 139.9, 145.7, 155.8, 168.8, 177.7, 186.2.

EXAMPLE 4

Compound I-b

Compound I-b (11-O-methyl-17-(2-dimethylaminoethyl)amino-17-demethoxygeldanamycin) was made following the general procedure of Method A. ESI TOF MS m/z 631.3692; calcd for $C_{33}H_{51}N_4O_8$ $[M+H]^+$, 631.3701. $^{13}C$ NMR (CDCl$_3$, 100 MHz) δ (relative to CDCl$_3$ at 77.0 ppm) 12.3, 14.1, 16.4, 21.6, 30.4, 33.6, 33.9, 36.4, 42.5, 44.8, 56.1, 57.4, 57.5, 59.8, 78.7, 79.5, 82.1, 83.5, 108.0, 108.7, 125.9, 127.8, 130.0, 132.1, 134.8, 136.4, 140.7, 145.1, 155.9, 168.7, 179.3, 184.4.

EXAMPLE 5

Compound I-c

Compound I-c (1-O-methyl-17-(2-fluoroethyl)amino-17-demethoxygeldanamycin) was made by both the general procedures of Method A and Method B: ESI TOF MS m/z 628.3030; calcd for $C_{31}H_{44}N_3O_8Na[M+Na]^+$, 628.3005. $^{13}C$ NMR (CDCl$_3$, 100 MHz) δ 12.2, 14.0, 16.3, 21.4, 30.5, 33.6, 33.8, 36.3, 45.5 (d, $^2J_{C,F}$=20 Hz), 56.0, 57.4, 59.6, 78.7, 79.3, 81.6 (d, $^1J_{C,F}$=171 Hz), 81.8, 83.2, 108.0, 109.6, 125.7, 127.9, 129.6, 132.1, 134.5, 136.5, 140.4, 144.5, 155.9, 168.6, 180.0, 183.9.

EXAMPLE 6

Compound I-d

Compound I-d (11-O-methyl-17-(2-(1-aziridinyl)ethyl)amino 17\demethoxygeldanamycin) was made following the general procedure of Method A: ESI TOF MS m/z 629.3529; calcd for $C_{33}H_9NO_8$ $[M+H]+$, 629.3545. $^{13}C$ NM (CDCl$_3$, 100 MHz) δ (relative to CDCl$_3$ at 77.0 ppm) 184.2, 179.6, 168.7, 155.9, 144.9, 140.7, 136.4, 134.7, 132.1, 130.0, 127.9, 125.8, 108.6, 107.9, 83.4, 81.9, 79.5, 78.8, 60.0, 59.7, 57.5, 56.1, 45.2, 36.4, 33.8, 33.4, 30.5, 27.3, 27.1, 21.5, 16.3, 14.0, 12.2.

EXAMPLE 7

Compound I-f

Compound 1-f (11-O-methyl-17-amino-17-demethoxygeldanamycin) was made by the both the general procedures of Method A and Method B: ESI TOF MS m/z 582.2821, calcd for $C_{29}H_{41}N_3O_8Na[M+Na]^+$, 582.2786. $^{13}C$ NMR (CDCl$_3$, 100 MHz) δ (relative to CDCl$_3$ at 77.0 ppm) 12.2, 13.9, 15.9, 22.2, 29.7, 32.9, 33.6, 36.3, 56.3, 57.5, 59.4, 79.0, 79.6, 81.6, 83.1, 108.0, 110.4, 125.9, 128.1, 130.4, 132.1, 134.6, 136.5, 140.1, 145.6, 155.9, 168.6, 179.6, 183.4.

EXAMPLE 8

Compound I-g

Compound I-g (11-O-methyl-17-allylamino-17-demethoxygeldanamycin) was made by both the general procedures of Method A and Method B: ESI TOF MS m/z 622.3090, calcd for $C_{32}H_{45}N_3O_8Na[M+Na]^+$, 622.3099. $^{13}C$ NMR (CDCl$_3$, 100 MHz) δ (relative to CDCl$_3$ at 77.0 ppm) 12.2, 13.9, 16.2, 21.4, 30.5, 33.5, 33.7, 36.3, 47.4, 56.1, 57.4, 59.5, 78.9, 79.5, 81.8, 83.2, 107.9, 108.8, 117.9, 125.8, 127.9, 129.9, 132.2, 132.9, 134.6, 136.4, 140.7, 144.4, 155.9, 168.6, 179.9, 184.1.

EXAMPLE 9

Compound I-h

Compound I-h (11-O-methyl-17-(2-(4-imidazolyl)ethyl)amino-17-demethoxygeldanamycin) was made by the general procedure of Method A: ESI TOF MS m/z 654.3529, calcd for $C_{34}H_{48}N_5O_8[M+H]^+$, 654.3497. $^{13}C$ NMR (CDCl$_3$, 100 MHz) δ (relative to CDCl$_3$ at 77.0 ppm) 12.3, 14.0, 16.3, 21.4, 27.8, 30.6, 33.5, 33.8, 36.3, 45.1, 56.2, 57.6, 59.6, 78.9, 79.6, 81.9, 83.3, 107.9, 108.8, 114.7, 125.9, 127.9, 129.9, 132.2, 134.7, 135.4, 136.1, 136.5, 140.8, 144.9, 155.9, 168.7, 179.5, 184.3.

EXAMPLE 10

Compound I-i

Compound I-i (11-O-methyl-17-(2-(1-azetidinyl)ethyl)amino-17-demethoxygeldanamycin) was made by the general procedure of Method A: ESI TOF MS m/z 643.3716, calcd for $C_{34}H_{51}N_4O_8[M+H]^+$, 643.3701. °C. NMR (CDCl$_3$, 100 MHz) δ (relative to CDCl$_3$ at 77.0 ppm) 12.2, 14.0, 16.3, 17.6, 21.5, 30.5, 33.5, 33.8, 36.4, 43.0, 55.0, 56.1, 57.5, 57.8, 59.6, 78.8, 79.5, 81.9, 83.4, 107.9, 108.6, 125.8, 127.8, 129.9, 132.1, 134.7, 136.4, 140.7, 145.1, 155.9, 168.7, 179.3, 184.3.

EXAMPLE 11

Compound I-i

Compound I-j (11-O-methyl-17-(2-(1-pyrrolidinyl)ethyl)amino-17-demethoxygeldanamycin) was prepared by the general procedure of Method A: ESI TOF MS m/z 657.3846, calcd for $C_{35}H_{53}N_4O_8[M+H]^+$, 657.3858. $^3C$ NMR (CDCl$_3$, 100 MHz) δ (relative to CDCl$_3$ at 77.0 ppm) 12.2, 13.9, 16.2, 21.5, 23.5, 30.5, 33.3, 33.7, 36.3, 43.7, 53.5, 54.1, 56.1, 57.4, 59.6, 78.8, 79.5, 81.8, 83.3, 107.9, 108.6, 125.8, 127.8, 130.0, 132.1, 134.7, 136.4, 140.6, 145.2, 155.9, 168.6, 179.1, 184.4.

EXAMPLE 12

Biological Activity

Hsp90 binding was determined according to the procedure of Carreras et al., *Anal. Biochem.*, 317 (1), 40–46 (June 2003), "Filter Binding Assay for the Geldanamycin-Heat Shock Protein 90 Interaction."

Cytotoxicity was determined with SKBr3 cells (ATCC HTB-30), a breast cancer cell line. The SKBr3 cells were maintained in McCoy's 5A modified medium (Invitrogen #16600082) with 10% fetal bovine serum (Hyclone #SH30070.03) and 2 mM L-glutamine at 37° C. in a humidified incubator with 5% carbon dioxide atmosphere. Cells were plated into 96-well microtiter back plates at 4,000 cells per 50 µL per well, overnight. Serial 10× dilutions of test compound (10 µM to 0.1 pM) in cell culture media were prepared with a Biomek 2000 apparatus, using the protocols of deeper-1000 µL-media and deeper-1000 µL-dilution. 50 µL of each dilution was added to wells containing cells. Each compound or control (medium only) was tested in duplicate. For each assay, the wells contained a final volume of 100 µL (50 µL of cells and 50 µL of compound dilution). After incubating for 72 h, the plates were let stand at room temperature for 30 min. CellTiter-Glo Luminescent Reagent (Promega #G7573) (100 µL) was added to each well. The well contents were mixed for 5 min and the plates were kept at room temperature for another 30 min. Luminescence was recorded using a Wallac VICTOR$^2$ Multilabel Counter (PerkinElmer) and $IC_{50}$ values were determined using Kaleidagraph software (Synergy Software).

Hsp90 binding and cytotoxicity data for compound I-a through I-j, together with data for geldanamycin itself, are presented in Table 2.

TABLE 2

| Compound | Hsp90 Binding ($K_d$, µM) | Cytotoxicity against SKBr3 Cells ($IC_{50}$, nM) |
| --- | --- | --- |
| I-a | 4 | 24 |
| I-b | 0.8 | 12 |
| I-c | 2.3 | 250 |
| I-d | 2.1 | 36 |
| I-e | 0.49 | 9.1 |
| I-f | 0.32 | 84 |
| I-g | 2.8 | 280 |
| I-h | 2.0 | 60 |
| I-i | 0.96 | 130 |
| I-J | 0.96 | 160 |
| Geldanamycin (comparative) | 0.5 | 23 |

The data show that compounds of this invention exhibit significant Hsp90 binding activity and cytotoxicity towards SKBr3 cells. In a preferred embodiment, compounds of this invention have a $K_d$ for Hsp90 binding of 4 µM or less. In another preferred embodiment, compounds of this invention have an $IC_{50}$ towards SKBr3 cells of 300 nM or less.

Additional data demonstrating the effectiveness of compounds of this invention against other types of cancer cells is provided in Table 3. (MCF-7 is another human breast cancer line. SKOV-3 is a human ovarian cancer cell line. A-549 is a human lung cancer line. CCRF-CEM, CCRF-CEM/taxol, CCRF-CEM/VBL, and CCRF-CEM/VP-16 are leukemia cell lines, the latter three being sublines resistant to paclitaxel, vinblastine, and VP-16 (etoposide), respectively.)

TABLE 3

| | Compound Cytotoxicity ($IC_{50}$, nM) | | | | | | | |
| --- | --- | --- | --- | --- | --- | --- | --- | --- |
| Cell Line | I-a | I-b | I-c | I-f | I-g | I-h | I-i | I-j |
| MCF-7 | 63 | 50 | 58 | 350 | 760 | 160 | 51 | 76 |
| SKOV-3 | 110 | 43 | 460 | 200 | 1300 | 320 | 65 | 69 |
| A-549 | 29 | 23 | 67 | 37 | 360 | 420 | 26 | 62 |

TABLE 3-continued

| | Compound Cytotoxicity ($IC_{50}$, nM) | | | | | | | |
| --- | --- | --- | --- | --- | --- | --- | --- | --- |
| Cell Line | I-a | I-b | I-c | I-f | I-g | I-h | I-i | I-j |
| CCRF-CEM | 420 | 58 | 960 | 250 | 2500 | 510 | 85 | 160 |
| CCRF-CEM/taxol | 2500 | 390 | 2700 | 850 | 3500 | 3000 | 510 | 520 |
| CCRF-CEM/VBL | 2500 | 960 | 2500 | 2500 | >5000 | >5000 | 2500 | 2500 |
| CCRF-CEM/VP-16 | 1400 | 65 | 2500 | 530 | 4000 | 2500 | 140 | 170 |
| HL-60/MX2 | 600 | 62 | 440 | 930 | 3000 | 2500 | 110 | 98 |

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

We claim:

1. A compound having a structure according to formula I-j

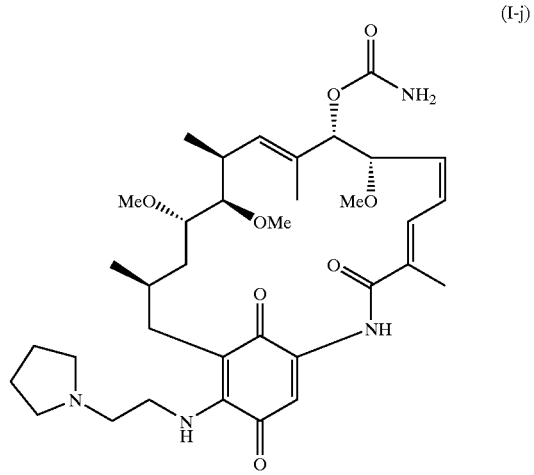

(I-j)

or the pharmaceutically acceptable salts thereof.

* * * * *